United States Patent [19]

Taguchi et al.

[11] Patent Number: 5,198,423
[45] Date of Patent: Mar. 30, 1993

[54] FUNCTIONAL POLYPEPTIDE CONTAINING A CELL BINDING DOMAIN AND A HEPARIN BINDING DOMAIN OF FIBRONECTIN

[75] Inventors: Yuki Taguchi, Otsu; Yoh'ichi Ohdate, Amagasaki; Yasutoshi Kawase, Otsu; Shouichi Goto, Tushima; Fusao Kimizuka, Ohmihachiman; Ikunoshin Kato, Uji; Ikuo Saiki; Ichiro Azuma, both of Sapporo, all of Japan

[73] Assignee: Takara Shuzo Co., Ltd., Kyoto, Japan

[21] Appl. No.: 526,733

[22] Filed: May 22, 1990

[30] Foreign Application Priority Data

May 26, 1989 [JP] Japan ................................. 1-131453
Dec. 1, 1989 [JP] Japan ................................. 1-310536

[51] Int. Cl.$^5$ ..................... C07K 15/12; C07K 15/14
[52] U.S. Cl. ......................................... 514/12; 514/8; 530/380; 530/350; 530/395; 435/69.7; 435/69.6
[58] Field of Search ...................... 530/380, 395, 350; 435/69.7, 69.6; 514/8, 12

[56] References Cited

U.S. PATENT DOCUMENTS 4,478,829 10/1984 Landaburu et al. ................ 424/177
5,045,631 9/1991 Kimizuka et al. ................... 530/350

FOREIGN PATENT DOCUMENTS 0207751 1/1987 European Pat. Off. .
0329413 8/1989 European Pat. Off. .
WO/08666 9/1989 PCT Int'l Appl. .

OTHER PUBLICATIONS

Kornblihto et al. 1985, The EMBO J. 4(7):1755–1759.
Folkman et al. 1987, Science 235:442–447.
Morton et al. 1987, Molecular and Cellular Biology 7(12):4297–4307.
Paolella et al. 1988, Nucleic Acids Research 16(8):3545–3557.
Obara et al., Cell, 53, 649 (1988).
Savill et al., Anticancer Res., 6, 323 (1986).
Segiuchi et al., Biochemistry, 25, 4936 (1986).
Rouslahti, Ann. Rev. Biochemn., 57, 375 (1988).

Primary Examiner—Robert A. Wax
Assistant Examiner—Keith C. Furman
Attorney, Agent, or Firm—Armstrong & Kubovcik

[57] ABSTRACT

This invention relates to a functional polypeptide containing the binding domain of human fibronectin and the heparin-binding domain of human fibronectin.

2 Claims, 3 Drawing Sheets

FUNCTIONAL POLYPEPTIDE CONTAINING A CELL BINDING DOMAIN AND A HEPARIN BINDING DOMAIN OF FIBRONECTIN

BACKGROUND OF THE INVENTION

1. Field of the Invention

This invention relates to a novel functional polypeptide, and, in particular, to a novel functional polypeptide which contains the cell-binding domain peptide of human fibronectin and the heparin-binding domain peptide of human fibronectin, to a method for its preparation; and also to the use of such functional polypeptide to inhibit angiogenesis.

2. Prior Art

Fibronectin (hereinafter referred to as FN) is a glycoprotein found in the plasma and extracellular matrix and has a number of functions (Annu. Rev. Biochem., 57, 375–413, 1988). Natural FN has been tested for use in pharmaceutical products such as in the treatment of wounds and in eye drops and also for use in cosmetics, but because natural FN is obtained from blood, its supply is limited, and its cost is high. In addition, because it may be contaminated with pathogenic bacteria and viruses, it is not in practical use at the present. For the same reasons, the functional domain of FN has not been isolated for use in practical applications.

Angiogenesis, which is the growth of new blood vessels, including capillaries, is known to be related to the progress of the disease in disorders such as chronic inflammations, certain immune reactions, and carcinogenesis. For that reason, a substance which inhibits angiogenesis may be able to largely inhibit the growth of tumors, the progress of retinopathy and chronic articular rheumatism, the spreading of foci of psoriasis, and the like.

Up to the present, steroids including prednisolone, 6α-methylprednisolone, and dexamethasone have been found to inhibit angiogenesis induced experimentally in chick embryo chorions, rabbit corneas, and hamster cheek pouches.

In FN there are two regions which bind with heparin (hereinafter referred to as heparin-binding domains), one of which is near the N-terminal and Ca ions are needed for binding at this domain. The other region is near the C-terminal, and the activity in the binding of this region to heparin is greater than the binding activity of the N-terminal region, with Ca ions having no effect on binding.

Recent research has shown that the heparin-binding domain of FN is important in the attachment, spreading, and movement of fibroblasts, endothelial cells, and certain kinds of tumor cells, just as the cell-binding domain is important. The heparin-binding domain of FN binds with the proteoglycans on the surface of the cells, and gives rise to interactions between the cell and extracellular matrix, thus contributing to cell attachment, spreading, and movement. Therefore, a polypeptide with both of the functions of cell-binding activity and heparin-binding activity can be expected to be of use in pharmaceutical preparations and the like by contributing to the healing of wounds by binding in the region of the wound with both cells and the extracellular matrix, and also by helping to maintain the normal condition.

The object of this invention is to provide a novel functional polypeptide which has both the functions of the cell-binding activity of FN and the heparin-binding activity of FN, to provide a method for the preparation of such a functional polypeptide, and to provide a novel agent for the inhibition of angiogenesis which makes use of a substance which is related to substances in the body and which is safe.

BRIEF SUMMARY OF THE INVENTION

Briefly, this invention relates to a novel functional polypeptide which has the cell-binding domain of human fibronectin bound directly or by means of a linker amino acid or peptide with the heparin-binding domain of human FN. This invention also relates to a recombinant plasmid which contains DNA coding for this functional polypeptide. This invention also relates to a transformant which carries such recombinant plasmid. Further, the invention also relates to a method for the preparation of the novel functional polypeptide, which comprises the cultivation of the transformant mentioned above, followed by the recovery of the functional polypeptide from the culture medium of the transformant. The present invention also relates to an agent for the inhibition of angiogenesis, containing the functional polypeptide mentioned above.

We have made a research work on the structure and the method of preparation of a novel polypeptide which has both cell-spreading activity and heparin-binding activity, and succeeded by the use of genetic engineering, in the production of a novel functional polypeptide which contains the cell-binding domain of human fibronectin bound directly or by means of a linker amino acid or peptide with the heparin-binding domain of human FN. The results of measurements of the biological activities of this novel functional polypeptide showed that the polypeptide has both the activities of cell spreading and of binding with heparin. It has also been found that when baby hamster kidney (BHK) cells and normal rat kidney (NRK) cells are used in the test, the cell-spreading activity is stronger than the case where there is only the cell-binding domain present. It has also been found that this functional polypeptide strongly inhibits angiogenesis. The present invention is based on these findings.

BRIEF DESCRIPTION OF THE DRAWINGS

This invention will be explained below in detail, by referring partly to the accompanying drawings wherein.

DETAILED DESCRIPTION OF THE INVENTION

The structure of the gene which codes for human FN has been reported in EMBO J., 4, 1755–1759 (1985). The cDNA clones (pLF2, pLF3, pLF4, and pLF5) which code for the cell-binding domain and the heparin-binding domain have also been described in Biochemistry, 25, 4936–4941, (1986). We have developed and applied for a patent (Japanese Laid-Open Patent Application 206998/89) for a polypeptide with cell-spreading activity and obtained from *Escherichia coli* cells that carry an expression vector attached to the fragment of cDNA which corresponds to the cell-binding domain, which fragment was obtained from pLF5. The cDNA coding for the cell-binding domain which is needed in this invention can be that of the recombinant plasmid disclosed in Japanese Laid-Open Patent Application 206998/89, which plasmid was named pTF7021. pTF7021 is a plasmid which expresses the amino acid sequence $Pro^{1239}$-$Met^{1517}$ (279 amino acids) of FN. By the introduction of, for example, the Nco I site, immediately before the termination codon of the translation region at the C-terminal of pTF7021, it is possible to link the cDNA of the cell-binding domain and the cDNA of another domain.

As one example of the novel functional polypeptide of this invention, there is the polypeptide of the following structural formula [I]:

$$C_{277}\text{-}(Met)_n\text{-}H_{271}\text{-}X \qquad [I]$$

wherein $C_{277}$ is the sequence of 277 amino acids which corresponds to $Pro^{1239}$-$Ser^{1515}$ of the cell-attachment domain of human FN; which sequence is represented by the formula [II]:

1239 [II]
Pro Thr Asp Leu Arg Phe Thr Asn Ile Gly

Pro Asp Thr Met Arg Val Thr Trp Ala Pro

Pro Pro Ser Ile Asp Leu Thr Asn Phe Leu

Val Arg Tyr Ser Pro Val Lys Asn Glu Glu

Asp Val Ala Glu Leu Ser Ile Ser Pro Ser

Asp Asn Ala Val Val Leu Thr Asn Leu Leu

Pro Gly Thr Glu Tyr Val Val Ser Val Ser

Ser Val Tyr Glu Gln His Glu Ser Thr Pro

Leu Arg Gly Arg Gln Lys Thr Gly Leu Asp

Ser Pro Thr Gly Ile Asp Phe Ser Asp Ile

Thr Ala Asn Ser Phe Thr Val His Trp Ile

Ala Pro Arg Ala Thr Ile Thr Gly Tyr Arg

Ile Arg His His Pro Glu His Phe Ser Gly

Arg Pro Arg Glu Asp Arg Val Pro His Ser

Arg Asn Ser Ile Thr Leu Thr Asn Leu Thr

Pro Gly Thr Glu Tyr Val Val Ser Ile Val

Ala Leu Asn Gly Arg Glu Glu Ser Pro Leu

Leu Ile Gly Gln Gln Ser Thr Val Ser Asp

Val Pro Arg Asp Leu Glu Val Val Ala Ala

Thr Pro Thr Ser Leu Leu Ile Ser Trp Asp

Ala Pro Ala Val Thr Val Arg Tyr Tyr Arg

Ile Thr Tyr Gly Glu Thr Gly Gly Asn Ser

Pro Val Gln Glu Phe Thr Val Pro Gly Ser

Lys Ser Thr Ala Thr Ile Ser Gly Leu Lys

Pro Gly Val Asp Tyr Thr Ile Thr Val Tyr

Ala Val Thr Gly Arg Gly Asp Ser Pro Ala

Ser Ser Lys Pro Ile Ser Ile Asn Tyr Arg

1515
Thr Glu Ile Asp Lys Pro Ser and wherein $H_{271}$ is the sequence of 271 amino acids which corresponds to the $Ala^{1690}$-$Thr^{1960}$ of the heparin-binding domain of human FN; which sequence is represented by the formula [III]:

1690 [III]
Ala Ile Pro Ala Pro Thr Asp Leu Lys Phe

Thr Gln Val Thr Pro Thr Ser Leu Ser Ala

Gln Trp Thr Pro Pro Asn Val Gln Leu Thr

Gly Tyr Arg Val Arg Val Thr Pro Lys Glu

Lys Thr Gly Pro Met Lys Glu Ile Asn Leu

Ala Pro Asp Ser Ser Ser Val Val Val Ser

Gly Leu Met Val Ala Thr Lys Tyr Glu Val

Ser Val Tyr Ala Leu Lys Asp Thr Leu Thr

Ser Arg Pro Ala Gln Gly Val Val Thr Thr

Leu Glu Asn Val Ser Pro Pro Arg Arg Ala

Arg Val Thr Asp Ala Thr Glu Thr Thr Ile

Thr Ile Ser Trp Arg Thr Lys Thr Glu Thr

Ile Thr Gly Phe Gln Val Asp Ala Val Pro

Ala Asn Gly Gln Thr Pro Ile Gln Arg Thr

Ile Lys Pro Asp Val Arg Ser Tyr Thr Ile

Thr Gly Leu Gln Pro Gly Thr Asp Tyr Lys

Ile Tyr Leu Tyr Thr Leu Asn Asp Asn Ala

Arg Ser Ser Pro Val Val Ile Asp Ala Ser

Thr Ala Ile Asp Ala Pro Ser Asn Leu Arg

Phe Leu Ala Thr Thr Pro Asn Ser Leu Leu

Val Ser Trp Gln Pro Pro Arg Ala Arg Ile

Thr Gly Tyr Ile Ile Lys Tyr Glu Lys Pro

Gly Ser Pro Pro Arg Glu Val Val Pro Arg

Pro Arg Pro Gly Val Thr Glu Ala Thr Ile

Thr Gly Leu Glu Pro Gly Thr Glu Tyr Thr

Ile Tyr Val Ile Ala Leu Lys Asn Asn Gln

Lys Ser Glu Pro Leu Ile Gly Arg Lys Lys

1960
Thr wherein X has the following formula [IV]:

Asp—Glu—Leu—Pro—Gln—Leu—Val—Thr—Leu—Pro— [IV]

His—Pro—Asn—Leu—His—Gly—Pro—Glu—Ile—Leu—

Asp—Val—Pro—Ser—Thr [IV]

or a peptide structure which has lost one portion or all of these residues, and wherein Met represents a methionine residue, and n is either 1 or zero.

In this specification, the numbers used to label the amino acids are the number of the amino acid residue from the N-terminal of the amino acid sequence obtained by translation of the cDNA sequence of FN in the EMBL Data Bank.

The heparin-binding domain has been obtained in fragments from decomposition with the use of trypsin, thermolysin, cathepsin D, etc. The sizes reported for the fragments are from 29 to 38 kDa. The domain has not been identified in detail, but it is generally believed to consist of three type III repeating sequences which are made of about 90 amino acids each attached to a part of the IIIcs sequence. The X of the structure formula [I] of this invention corresponds to one portion of the IIIcs sequence. The IIIcs sequence is not required for heparin-binding activity, but it seems that the IIIcs sequence is needed for attachment to certain kinds of lymphocytes. We have brought about the expression of a fragment which contains three repeats of the type III sequence (the $H_{271}$ of the structural formula [I] of this invention corresponds to these three repeats) and also of a fragment which contains one portion of the IIIcs sequence (the $H_{271}$-X of the structural formula [I] of this invention) in $E.$ $coli$ and measured the heparin-binding activity and the cell-binding activity obtained in these two cases. The results showed that both fragments had both heparin-binding activity and cell-binding activity when BHK cells were used in the test. The cell-binding activity means both cell-attachment activity and cell-spreading activity. The cell-attachment and cell-spreading activities of the $H_{271}$-X fragment were stronger than those of the $H_{271}$ fragment.

Figure 1:
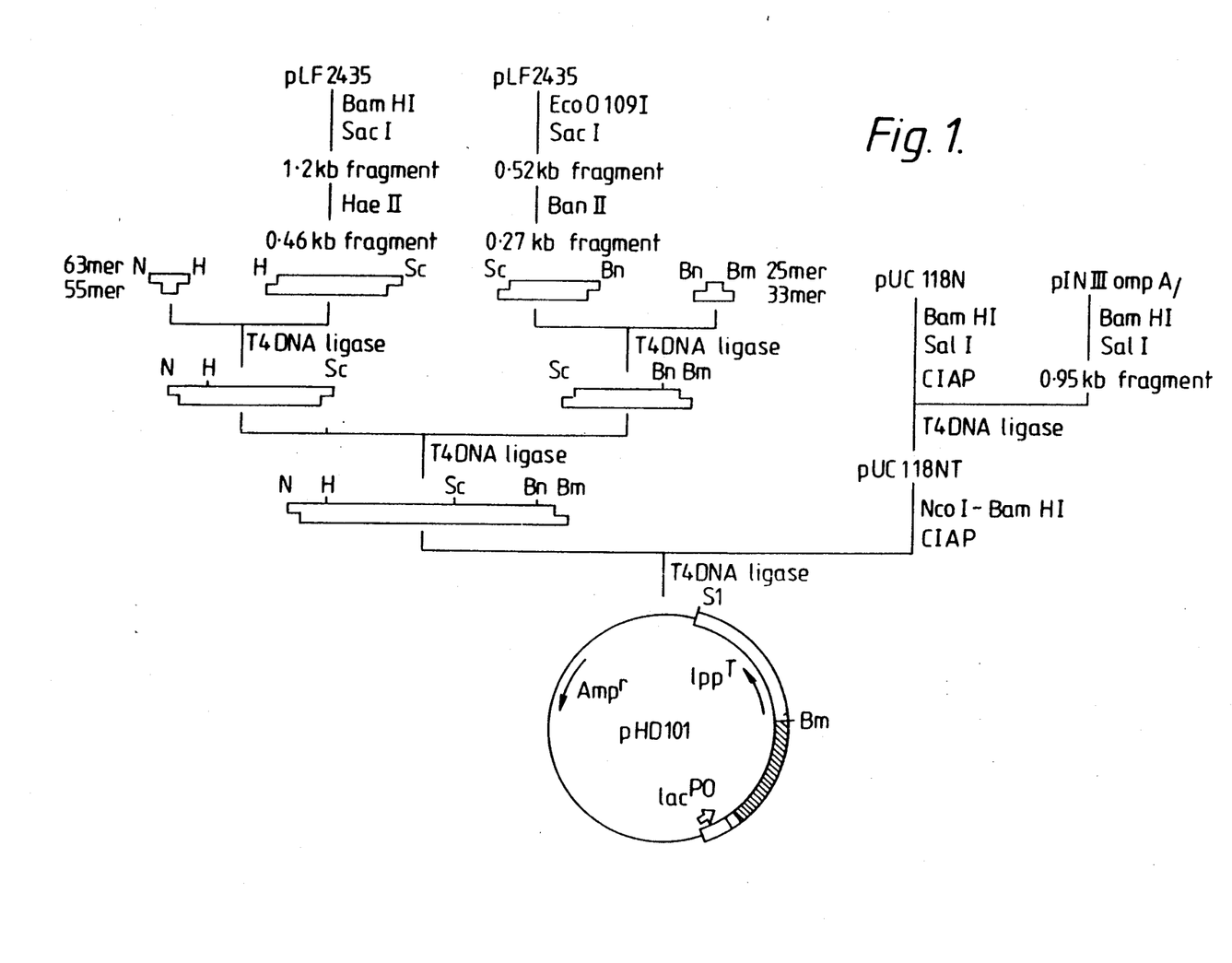
FIG. 1 is a figure showing the process of construction of the plasmid pHD101 which expresses H-271.

The cDNA which codes for the heparin-binding domain can be extracted from pLF2435. pLF2435 is a plasmid that was obtained by the reconstruction of the plasmids pLF2, pLF3, pLF4 and pLF5 mentioned above, and this reconstructed plasmid contains the cDNA which codes for the heparin-binding domain of FN. However, the cDNA which corresponds to the IIIcs portion is not contained in this plasmid, and it is necessary to construct a DNA sequence corresponding to X by means of chemical synthesis. The cDNA fragment needed can be cleaved from pLF2435 by the use of restriction enzymes. With the use of DNA ligase, synthetic DNA which contains the initiation codon can be ligated on the 5' end of the cDNA fragment, and synthetic DNA which contains the termination codon can be ligated on the 3' end of the cDNA fragment. Then, by connection with an appropriate expression vector, it is possible to obtain a plasmid which expresses a polypeptide having three repeats of the type III repeating sequence (refer to FIG. 1). FIG. 1 is a figure showing the process of the construction of the plasmid pHD101 which expresses $H_{271}$.

Figure 2:
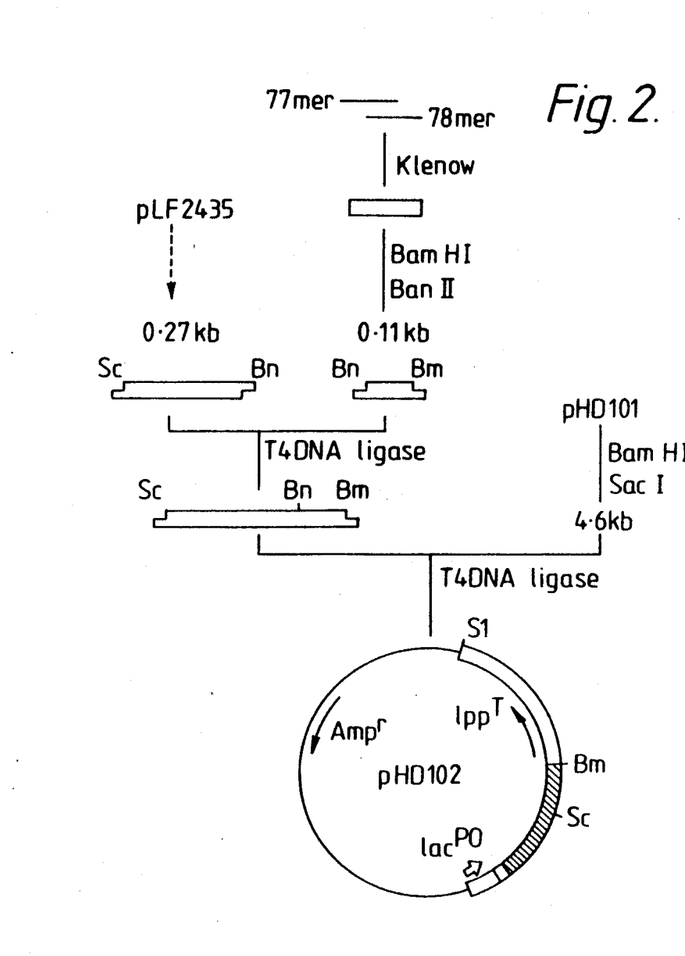
FIG. 2 is a figure showing the process of construction of the plasmid pHD102 which expresses H-296.

By the incorporation of the plasmid to the chemically synthesized DNA corresponding to X, which is one portion of IIIcs, it is possible to obtain a plasmid which expresses a peptide containing IIIcs (refer to FIG. 2). FIG. 2 is a figure showing the process of the construction of the plasmid pHD102 which expresses $H_{296}$.

Figure 3:
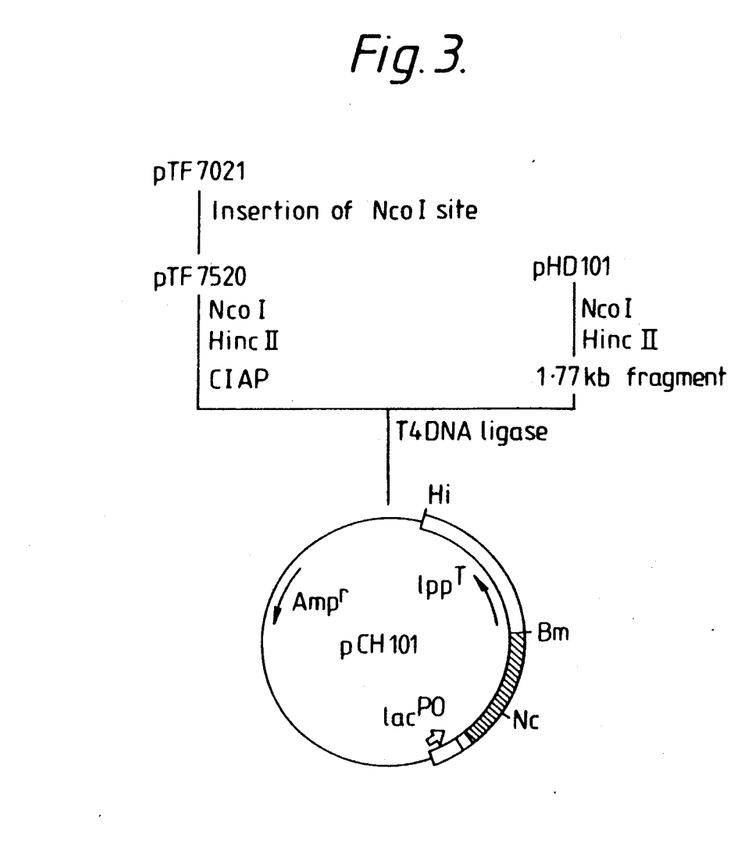
FIG. 3 is a figure showing the process of construction of the plasmid pCH101 which expresses $C_{277}$-Met-$H_{271}$.
Figure 4:
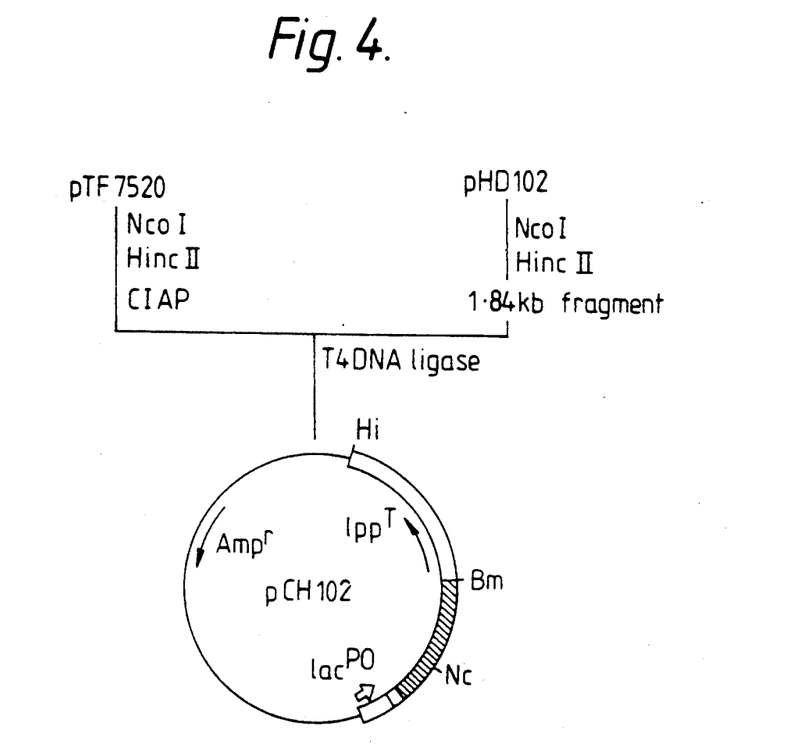
FIG. 4 is a figure showing the process of construction of the plasmid pCH102 which expresses $C_{277}$-Met-$H_{296}$.

Satisfactory results can be obtained by the use of any of the expression vectors which are known, including, for example, pUC118N/pUC119N, described in FEBS Lett. (223, 174–180, 1987) and derivatives thereof. By the introduction of such a plasmid into $E.$ $coli$ cells, it is possible to bring about the expression of a polypeptide with heparin-binding activity, and it is possible to investigate the properties of such a polypeptide. Next, cDNA fragments can be extracted from these plasmids, and linked at the NcoI site at the 3' end of the translation region of the plasmid pTF7520 that is constructed from the plasmid pTF7021 mentioned above, by which means it is possible to obtain a recombinant plasmid which expresses a polypeptide containing the cell-binding domain of human FN bound directly on by means of a linker amine acid or peptide with the heparin binding domain of human FN (refer to FIGS. 3 and 4). FIG. 3 is a figure showing the process of the construction of plasmid pCH101 which expresses $C_{277}$-Met-$H_{271}$, and FIG. 4 is a figure showing the process of the construction of the plasmid pCH102 which expresses $C_{277}$-Met-$H_{296}$.

The portion of connection in the plasmids mentioned above can include DNA which codes for a methionine residue which originated from the NcoI site and is used as a linker. The effects of this invention are not affected by the presence or absence of a linker. If necessary, it is possible to remove the linker with ease by site-directed mutagenesis.

The plasmid thus obtained is introduced into $E.$ $coli$ cells, and the cells are cultured under appropriate conditions, by which means the desired peptide accumulates in the cells of $E.$ $coli$. Immunoblotting can be used to check for the expression of the polypeptide. After the separation of the whole-cell protein of the recombinant $E.$ $coli$ cells by the use of SDS-polyacrylamide electrophoresis (PAGE), the electrophoresis pattern is transferred to a nitrocellulose membrane. The band which is detected by both a monoclonal antibody, FN-10 (Takara Shuzo), which recognizes the cell-binding domain of FN and a monoclonal antibody, either IST-1 or IST-2 (Sera-Lab), which recognizes the heparin-binding domain of FN is the desired polypeptide.

The desired polypeptide can be purified, for example, in the following way. Recombinant $E.$ $coli$ cells are cultured in a medium such as L-broth and the cells are collected and treated by sonication. The sonicated cell extract is centrifuged, and the supernatant is obtained. The supernatant is first dialyzed and then passed through a DEAE ion-exchange column. Then it is treated by CM ion-exchange chromatography and/or affinity chromatography on heparin-agarose, or the like.

The polypeptide thus obtained can be assayed for cell-spreading activity toward BHK or NRK cells and for heparin-binding activity. For the measurement of cell-spreading activity, the method of, for example, Ruoslahti et al. (Methods in Enzymology, 82, 803–831, 1981) can be used. In brief, the sample is first used to coat the wells of a microtitre plate, after which bovine serum albumin (BSA) is used for blocking, and then a suspension of BHK or NRK cells is added to the wells, and the plate is incubated for about 1 hour at 37° C. The unattached cells are removed by washing of the plate, and the remaining cells are fixed with formalin, after which the spreading of the cells is observed under a microscope. From the results, the strength of the cell-spreading activity can be calculated. For the measurement of heparin-binding activity, the sample is put on a column of, for example, AF-heparin Toyopearl (Tosoh Corp.) or some such carrier bound with heparin, so that the sample is adsorbed, and elution is done with a gradient of increasing NaCl concentrations. The salt concentration at which the sample is eluted can be used to express the strength of binding to heparin.

It can be found by the above measurement procedures that each polypeptide obtained has strong cell-spreading activity toward both BHK and NRK cells, and that it also has a strong affinity toward heparin.

The functional polypeptide of this invention has a strong effect in inhibiting angiogenesis, and it may be useful in helping to prevent metastasis and the growth of tumors, to cause some degree of regression in the size of tumors, to decrease the severity of osteoporosis, to inhibit the progress of retinopathy and chronic articular rheumatism, as an inhibitor of the spread of foci of psoriasis, and for other disorders or conditions related to angiogenesis.

When the functional polypeptide of this invention is to be used as a pharmaceutical preparation, it can be prepared in the ordinary way with suitable known carriers for use in pharmaceutical preparations, and taken by the oral or by other routes.

The amount of a single dose depends on the age, weight, and signs and symptoms of the patient, and also on the purpose of treatment, etc., but in general, a therapeutic dose by a non-oral route is 1–100 mg/kg per day and by the oral route, 5–500 mg/kg per day.

When C57BL/6 mice were used in a test of the toxicity of the functional peptide, no signs of toxicity were found when 100 mg/kg was given by intravenous injection.

This invention will be explained in more detail by reference to the following examples. However, this invention is not to be taken to be limited to these examples.

EXAMPLE 1

Cloning of cDNA fragment which codes for the heparin-binding domain of FN, Ala$^{1690}$-Thr$^{1960}$ (a sequence of 271 amino acids, hereinafter referred to as H-271; see FIG. 1):

(1-1) Preparation of Synthetic DNA Adapter

A DNA synthesizer from Applied Biosystems (model 380A) was used to synthesize adapters on the 5' end (chain length 63 or 55; see FIG. 1) and on the 3' end (chain length 25 or 33; see FIG. 1) to join the cDNA fragment coding for the heparin-binding domain to a vector. After 2 μg of each of these two preparations was phosphorylated on their 5' ends, annealing was done, resulting in a double strand.

(1-2) Preparation of NcoI-SacI Fragment

First, 100 μg of plasmid pLF2435 that is 5.9 kb long, and that contains the cDNA fragment coding for the H-271 of FN (Biochemistry, 25, 4936–4941, 1986) was digested with BamHI and SacI. Then the digest was treated by agarose gel electrophoresis, and the 1.2 kb fragment was obtained. This fragment was further digested with HaeII, and the digest was treated by agarose gel electrophoresis, by which means 0.46 kb HaeII-SacI fragment was obtained. Then 700 ng of this fragment and 120 ng of the 5' end adapter from section 1-1 were mixed in 20 μl of a buffer for use with T4 DNA ligase containing 0.5 mM ATP, 10 mM dithiothreitol (DTT), and 2.8 units of T4 DNA ligase. The reaction mixture was incubated overnight at 16° C. Then the reaction mixture was heated at 65° C. for 10 minutes, digested with NcoI and SacI, and treated by agarose gel electrophoresis. In this way, about 120 ng of 0.52 kb NcoI-SacI fragment was obtained.

(1-3) Preparation of SacI-BamHI Fragment

First, 100 μg of the plasmid mentioned above, pLF2435, was digested with Eco0109I and SacI, and the digest was treated by agarose gel electrophoresis, to obtain a 0.52 kb fragment. This fragment was further digested with BanII, and the digest was treated by agarose gel electrophoresis, giving a 0.27 kb SacI-BanII fragment. Then 400 ng of this fragment and 80 ng of the 3' end adapter from section 1-1 were mixed in 20 μl of a buffer for use with T4 DNA ligase containing 0.5 mM ATP, 10 mM DTT and 2.8 units of T4 DNA ligase. The reaction mixture was incubated overnight at 16° C. Then the reaction mixture was heated at 65° C. for 10 minutes, digested with BamHI and SacI, and treated by agarose gel electrophoresis. In this way, about 65 ng of 0.30 kb SacI-BamHI fragment was obtained.

(1-4) Preparation of NcoI-BamHI Fragment

First, 120 ng of the NcoI-SacI fragment obtained in (1-2) and 65 ng of the SacI-BamHI fragment obtained in (1-3) were mixed in 20 μl of a buffer for use with T4 DNA ligase containing 0.5 mM ATP, 10 mM DTT and 2.8 units of T4 DNA ligase. The reaction mixture was incubated overnight at 16° C. Then it was heated at 65° C. for 10 minutes, and digested with BamHI and NcoI. The digest was treated by agarose gel electrophoresis, by which means about 28 ng of 0.82 kb NcoI-BamHI fragment was obtained.

(1-5) Construction of pUC118NT

First, 1 μg of the secretion expression vector pINIII-ompA$_1$ (EMBO J, 3, 2437–2442, 1984) was digested with BamHI and SalI, and the digest was treated by agarose gel electrophoresis, by which means 0.95 kb BamHI-SalI fragment containing the 1 pp terminator sequence was obtained. Then, 30 ng of this fragment was mixed with 30 ng of plasmid pUC118N which had been digested with BamHI and SalI and which had been dephosphorylated in 20 μl of a buffer for use with T4 DNA ligase containing 0.5 mM ATP, 10 mM DTT and 2.8 units of T4 DNA ligase. The reaction mixture was incubated overnight at 16° C., and 10 μl of the reaction mixture was used to transform cells of E. coli HB101, by which means there was obtained a plasmid carrying the lpp terminator sequence. The plasmid was designated pUC118NT.

Plasmid pUC118N was obtained by creation of an NcoI site surrounding the translation initiation codon of the commercially available vector pUC118 (Takara Shuzo). The distance between the initiation codon and the ribosome binding site was eight bases.

(1-6) Cloning of NcoI-BamHI Fragment in pUC118NT

First, 0.1 μg of the plasmid pUC118NT obtained in (1-5) was digested with NcoI and BamHI and dephosphorylated. Then 20 ng of this plasmid was mixed with 20 ng of the NcoI-BamHI fragment obtained in (1-4) in 20 μl of buffer for use with T4 DNA ligase containing 0.5 mM ATP, 10 mM DTT and 2.8 units of T4 DNA ligase. This reaction mixture was incubated overnight at 16° C., and then 10 μl of the reaction mixture was used to transform cells of E. coli HB101.

(1-7) Transformation of E. coli and Analysis of the Plasmid

Ten microliters of the reaction mixture obtained in (1-6) was used to transform cells of E. coli HB101. Of the recombinants obtained, the plasmids of 18 clones were analyzed. In this analysis, the alkali-lysis method was used to isolate plasmids. Then the plasmids were digested with BamHI and NcoI. The digest was treated by agarose gel electrophoresis. The band expected for the NcoI-BamHI fragment at 0.82 kb was searched for. One of the clones produced the desired band. The dideoxy method was used to identify the base sequence of the plasmid, and it was found that the desired sequence was present. This recombinant plasmid was designated pHD101.

E. coli HB101 carrying this plasmid was named E. coli HB101/pHD101, and was deposited at the Fermentation Research Institute of the Agency of Industrial Science and Technology, Japan, as FERM BP-2264.

(1-8) Purification of the Polypeptide from the Recombinant

First, cells of E. coli HB101/pHD101 that were obtained in (1-7) were cultivated overnight at 37° C. in a shaking test tube containing 5 ml of L-broth which contained ampicillin at the concentration of 50 $\mu$g/ml. The contents were used to inoculate 500 ml of the same broth in a Erlenmeyer flask with a 2 l capacity. This was cultured with agitation at 100 rpm. Then, when the absorbance at 660 nm reached 0.3, 2 mM isopropyl-$\beta$-thiogalactoside (IPTG) was added, and the cells were harvested after 20 hours more of cultivation. A portion of the collected cells was used in immunoblotting. Thus, whole-cell protein was separated on SDS-PAGE, and the electrophoretic pattern was transferred to a nitrocellulose membrane, after which a monoclonal antibody, IST-1 (Sera-Lab) which specifically recognizes the heparin-binding domain of FN was used as the first antibody, and peroxidase-labelled antibody as the second antibody. The peroxidase activity of the bound second antibody was assayed by staining in the presence of 4-chloro-1-naphthol and hydrogen peroxide, to check for production of the desired polypeptide in the vicinity of 29 kDa. Next, the whole-cell pellet was suspended in a mixture containing 20 mM $K_2HPO_4$ (pH 7.0), 1 mM EDTA, 5 mM mercaptoethanol, and 3 $\mu$M p-amidinophenyl-methanesulfonyl fluoride (p-APMSF), and the mixture was sonicated. Then the mixture was centrifuged for 20 minutes at 12000 rpm, and 25 ml of supernatant was obtained. The supernatant was passed through a 15 ml column of CM-Toyopearl 650M equilibrated with 20 mM $K_2HPO_4$ buffer (pH 7.0). The non-adsorbed fraction was washed through the column with the use of the same buffer, and then the column was eluted with 20 mM $K_2HPO_4$ buffer (pH 7.0) that contained 0.15M NaCl, and the eluate was collected in fractions. The eluate was used in immunoblotting, and desired fractions were collected from this step. Next, this fraction was passed through an 80 ml column of heparin-Toyopearl 650M equilibrated with 20 mM $K_2HPO_4$ (pH 7.0) that contained 0.15M NaCl. Then the column was washed with 20 mM $K_2HPO_4$ buffer (pH 7.0) that contained 0.2M NaCl, and eluted with a linear gradient of salt concentrations from 0.2M NaCl to 0.45M NaCl in the 20 mM $K_2HPO_4$ buffer (pH 7.0). The desired fractions were collected by immunoblotting, desalted, lyophilized, and found by electrophoresis to contain about 20 mg of almost homogeneous polypeptide. Then a peptide sequencer (Applied Biosystems 477A/120A) was used to identify the amino acid sequence of this peptide starting from the N-terminal. The sequence was found to be Ala-Ile-Pro-Ala-Pro-Thr-Asp-Leu. This was the same sequence from the N-terminal as that of the desired polypeptide. By digestion with carboxy-peptidase P (Takara Shuzo), threonine was found to be the C-terminal amino acid.

EXAMPLE 2

Cloning of the cDNA fragment which codes for the heparin-binding domain ($Ala^{1690}$-$Thr^{1985}$, an amino acid sequence of 296 residues, hereinafter referred to as H-296) which contains one portion ($Asp^{1961}$-$Thr^{1985}$, an amino acid sequence of 25 amino acids) of the IIIcs region of FN (see FIG. 2).

(2-1) Preparation of BanII-BamHI Fragment

With a DNA synthesizer (Applied Biosystems model 380A), DNA was synthesized which had a chain length of 77 or 78 bases (see FIG. 2) and which contained a DNA fragment coding for the CS1 region of IIIcs of FN (J. Cell Biol., 103, 2637-2647, 1986). Then, 2 $\mu$g of both strands were phosphorylated at the 5′ ends and next double-stranded DNA was made by the annealing of single stranded DNA with complementary sequences.

This DNA was mixed into 100 $\mu$l of a reaction mixture of 7 mM Tris-HCl (pH 7.5) containing 0.1 mM EDTA, 20 mM NaCl, 7 mM $MgCl_2$, 0.1 mM dATP, 0.1 mM dGTP, 0.1 mM dCTP, 0.1 mM dTTP, and 2 units of Klenow enzyme. The reaction mixture was incubated at 37° C. for 30 minutes. Then the reaction was stopped by heating the mixture at 70° C. for 5 minutes, and the reaction mixture was digested with BamHI and BanII. The digest was treated by agarose gel electrophoresis, and about 400 ng of 0.11 kb BanII-BamHI fragment was obtained.

(2-2) Preparation of SacI-BamHI Fragment

First, 200 ng of the BanII-BamHI fragment obtained in (2-1) and 490 ng of the 0.27 kb SacI-BanII fragment obtained in (1-3) were mixed in 20 $\mu$l of a reaction mixture of buffer for use with T4 DNA ligase containing 0.5 mM ATP, 10 mM DTT and 2.8 units of T4 DNA ligase. The reaction mixture was incubated overnight at 16° C. Then the reaction mixture was heated at 65° C. for 10 minutes and digested with BamHI and SacI. The digest was treated by agarose gel electrophoresis, giving about 100 ng of 0.38 kb SacI-BamHI fragment.

(2-3) Preparation of SacI-BamHI Fragment (Vector Fragment) of pHD101

First, 1 $\mu$g of plasmid pHd101, which codes for H-271, was digested with SacI and BamHI. The digest was dephosphorylated and treated by agarose gel electrophoresis, giving about 280 ng of 4.6 kb SacI-BamHI vector fragment.

(2-4) Linkage of SacI-BamHI Fragment and Vector

First, 50 ng of the 0.38 kb SacI-BamHI fragment obtained in (2-2) and 20 ng of the 4.6 kb SacI-HamHI vector obtained in (2-3) were mixed in 20 $\mu$l of a reaction mixture of buffer for use with T4 DNA ligase containing 0.5 mM ATP, 10 mM DTT and 2.8 units of T4 DNA ligase. The reaction mixture was incubated overnight at 16° C., and 10 μl of the mixture was then used to transform cells of E. coli HB101.

(2-5) Transformation of E. coli and Analysis of the Plasmids

As described above, 10 μl of the reaction mixture obtained in (2-4) was used to transform cells of E. coli HB101. Of the clones obtained from the recombinants, 12 clones were analyzed for plasmids. The alkali-lysis method was used to isolate plasmids. Then the plasmids were digested with BamHI and NcoI. The digest was treated by agarose gel electrophoresis. The band expected for the NcoI-BamHI fragment at 0.9 kb was searched for. One of the clones produced the desired band. The dideoxy method was used to identify the base sequence of this plasmid and it was found that the desired sequence was present. This recombinant plasmid was designated pHD102.

E. coli HB101 carrying this plasmid was named E. coli HB101/pHD102, and deposited at the Fermentation Research Institute of the Agency of Industrial Science and Technology, Japan as FERM P-10721.

(2-6) Purification of the Polypeptide from the Recombinant

By the method used in (1-8), cells of E. coli HB101/pHD102 obtained in (2-5) were cultured in 500 ml of culture broth, and from this culture broth, about 5 mg of polypeptide was obtained which was fairly homogeneous by electrophoresis. A peptide sequencer (Applied Biosystems 477A/120A) was used to identify the amino acid sequence of this peptide from the N-terminal. The sequence was found to be the same as that from the N-terminal sequence of the desired peptide. By digestion with carboxy-peptidase P, threonine was found to be the C-terminal amino acid.

EXAMPLE 3

Cloning of the cDNA fragment which codes for the fusion protein of $Pro^{1239}$-$Ser^{1515}$, the sequence of 277 amino acids of the cell-binding domain of FN, and H-271 (see FIG. 3):

(3-1) Construction of Plasmid which Codes for the $Pro^{1239}$-$Ser^{1515}$ Cell-binding Domain (with a Sequence of 277 Amino Acids)

A plasmid was constructed by the insertion of the NcoI site immediately in front of the termination codon of the translation region of the recombinant plasmid pTF7021 disclosed in Japanese Laid-Open Patent Application 206998/89 by site-directed mutagenesis. The oligo nucleotide d[pCTATTACACCATGGATGGTTTG] was synthesized and a kit (site-directed mutagenesis system Mutan-K; Takara Shuzo) was used to achieve insertion of the NcoI site into pTF7021. With this insertion of the NcoI site, the $Gln^{1516}$-$Met^{1517}$ of the C-terminal of the cell-binding domain was replaced by $Met^{1516}$-$Val^{1517}$ (see FIG. 3). The plasmid obtained was designated pTF7520.

(3-2) Preparation of the NcoI-HincII Fragment of pHD101

First, 1 μg of the recombinant plasmid pHD101 obtained in (1-7) was digested with NcoI and HincII, and the digest was treated with agarose gel electrophoresis, giving about 100 ng of 1.77 kb NcoI-HincII fragment.

(3-3) Cloning of the NcoI-HincII Fragment from pHD101 in pTF7520

First, the plasmid pTF7520 obtained in (3-1) was digested with NcoI and HincII and the digest was dephosphorylated. Then 50 ng of this fragment and 50 ng of the NcoI-HincII fragment obtained in (3-2) were mixed with 20 μl of a buffer for use with T4 DNA ligase containing 0.5 mM ATP, 10 mM DTT and 2.8 units of T4 DNA. This reaction mixture was incubated T overnight at 16° C. The 10 μl of the reaction mixture was used to transform cells of E. coli HB101. A plasmid was obtained that expressed the fusion protein $C_{277}$-Met-$H_{271}$ which was $Pro^{1239}$-$Ser^{1515}$, the sequence of 277 amino acids of the cell-binding domain of FN, bound via methionine to H-271. The plasmid was designated pCH101.

E. coli HB101 carrying this plasmid was named E. coli HB101/pCH101 and deposited at the Fermentation Research Institute of the Agency of Industrial Science and Technology, Japan, as FERM BP-2799.

(3-4) Removal of the Intervening Sequence ATG from pCH101

A methionine was added to the space between $Pro^{1239}$-$Ser^{1515}$, the sequence of 277 amino acids of the cell-bindning domain and H-271 giving the fusion protein $C_{277}$-Met-$H_{271}$ expressed by the plasmid pCH101 obtained in (3-3). The sequence, which corresponded to this methionine, ATG, was removed by site-directed mutagenesis. The oligonucleotide d[pAGGAATAGCGGATGGTTT] was synthesized and a site-directed mutagenesis system Mutan-K was used, resulting in the removal of the intervening sequence ATG.

A plasmid was obtained which expressed the fusion protein $C_{277}$-$H_{271}$, which consisted of $Pro^{1239}$-$Ser^{1515}$, the sequence of 277 amino acids of the cell-binding domain, bound directly to H-271. The plasmid was designated pCH201.

(3-5) Purification of the Polypeptide from the Recombinant

By the method described in (1-8), cells of E. coli HB101/pCH101 obtained in (3-3) were cultured in 500 ml of culture broth, and from this culture broth, a cell extract was obtained. The fractions which reacted with both a monoclonal antibody which recognized the cell-binding domain of FN (FN-10, Takara) and the monoclonal antibody IST-1 were purified by the methods of (1-8), and 15 mg of purified product was obtained. The sequence from the N-terminal of this peptide was identical with that of the desired peptide. By digestion with carboxypeptidase P, threonine was found to be the C-terminal amino acid.

EXAMPLE 4

Cloning of the cDNA fragment which codes for the fusion protein of $Pro^{1239}$-$Ser^{1515}$, the sequence of 277 amino acids of the cell-binding domain of FN, and H-296 (see FIG. 4):

(4-1) Preparation of the NcoI-HincII Fragment of pHD102

First, 1 μg of the recombinant plasmid pHD102 obtained in (2-5) was digested with NcoI and HincII, and the digest was treated by agarose gel electrophoresis, giving about 100 ng of 1.84 kb NcoI-HincII fragment.

(4-2) Cloning of NcoI-HincII Fragment from pHD102 in pTF7520

First, 1 μg of plasmid pTF7520 obtained in (3-1) was digested with NcoI and HincII, and the digest was dephosphorylated. Then 50 ng of this fragment and 50 ng of the NcoI-HincII fragment obtained in (4-1) were mixed with 20 μl of buffer for use with T4 DNA ligase that contained 0.5 mM ATP, 10 mM DTT, and 2.8 units of T4 DNA ligase. The reaction mixture was incubated overnight at 16° C., and then 10 μl of this reaction mixture was used to transform cells of $E.\ coli$ HB101. A plasmid was obtained which expressed the fusion protein $C_{277}$-Met-$H_{296}$ which was $Pro^{1239}$-$Ser^{1515}$, the sequence of 277 amino acids of the cell-binding domain of FN, bound via methionine to H-296. The plasmid was designated pCH102.

$E.\ coli$ HB101 carrying this plasmid was named $E.\ coli$ HB101/pCH102 and deposited at the Fermentation Research Institute of the Agency of Industrial Science and Technology, Japan, as FERM BP-2800.

(4-3) Removal of the Intervening Sequence ATG from pCH102

A methionine was added to the space between $Pro^{1239}$-$Ser^{1515}$, the sequence of 277 amino acids of the cell-binding domain, and H-296, giving the fusion protein $C_{277}$-Met-$H_{296}$ expressed by the plasmid pCH102 obtained in (4-2). The intervening sequence that corresponded to this methionine, ATG, was removed by the same methods as in (3-4). A plasmid was obtained that expressed the fusion protein $C_{277}$-$H_{296}$, which consisted of $Pro^{1239}$-$Ser^{1515}$, the sequence of 277 amino acids of the cell-binding domain bound directly to H-296. This plasmid was designated pCH202.

(4-4) Purification of the Polypeptide from the Recombinant

By the method described in (3-5), cells of $E.\ coli$ HB101/pCH102 obtained in (4-2) were cultured and purified in the same way as in (3-5). From the 500 ml of culture broth, about 6 mg of polypeptide that was fairly homogeneous by electrophoresis was obtained. Analysis of the N-terminal sequence and the C-terminal showed results which were identical to those expected for the desired peptide.

EXAMPLE 5

Measurement of Biological Activity

The polypeptides obtained in Examples 1-4 were assayed for cell-spreading activity and heparin-binding activity.

Cell-spreading activity was measured by the method of Ruoslahti et al. (Methods in Enzymology, 82, 803-831, 1981). The sample to be tested was dissolved in distilled water, phosphate-buffered saline (PBS), etc, and diluted stepwise in a 96-well microtitre plate. The volume used was 50 μl per well. The samples were incubated at 4° C. for 2 hours to allow the 3% BSA was added, and blocking was done by incubation of the plate at 37° C. for 1 hour. Then the wells were washed with PBS, and 100 μl of a suspension of baby hamster kidney cells, BHK-21, suspended at the concentration of 5×10⁵/ml in Dulbecco - modified Eagle medium, (DMEM) was put into each well. The BHK-21 cells had been stored frozen and were repeatedly cultured before being treated with trypsin at 37° C. for 5 min before use. The plate was then incubated at 37° C. for 1 hr. The plate was washed after being incubated with PBS, and the cells were fixed with 3% formalin.

Here, the $ED_{50}$ of the samples was defined as the concentration of the sample that gave 50% as many spread cells as the maximum number of spread cells produced when human FN was used at a high concentration. The spreading of BHK-21 cells was observed under a microscope and the $ED_{50}$ of each sample was calculated.

Heparin-binding activity was measured as follows. The sample was put on a 1.5 ml-column of AF-heparin-Toyopearl 650M equilibrated with 20 mM phosphate buffer (pH 7.0), and the NaCl concentration of the buffer was increased stepwise to elute the sample. The salt concentration at which elution occurred was used to express the heparin-binding activity.

The biological activities of the various samples, measured as described above, were as shown in Table 1.

TABLE 1

| Sample | Cell-spreading activity $ED_{50}$ (nmol/ml) | Heparin-binding activity (Salt conc., mM, for elution) |
| --- | --- | --- |
| H-271 | None | 300 |
| H-296 | 41 | 300 |
| $C_{277}$-Met-$H_{271}$ | 0.176 | 300 |
| $C_{277}$-Met-$H_{296}$ | 0.084 | 300 |

EXAMPLE 6

Inhibition of Angiogenesis

With three mice in each group, C57BL/6 mice were injected intradermally at two sites on the back with $5\times10^5$ cells of B16-BL6 melanome alone or else with a mixture of the same number of these cells with 100 μg of one of the polypeptides of this invention, $C_{277}$-Met-$H_{296}$. Three days after the injection, an i.v. injection (0.2 ml) of 1% Evans Blue was made, the mice were immediately killed, and the dorsal skin of the mice was separated from underlying tissues. Angiogenesis was evaluated by counting of the number of vessels oriented toward the tumor mass. The results are shown in Table 2.

TABLE 2

| | Numbers of vessels (mean ± SD) |
| --- | --- |
| Control mice | 19 ± 3 |
| Mice given $C_{277}$-Met-$H_{296}$ | 12 ± 1 |

EXAMPLE 7

To 30 parts by weight of the polypeptide $C_{277}$-Met-$H_{296}$, PBS was added for total weight of 2000 parts, and the solution was sterilized by filtration through a Millipore GS filter. Then 2 g of the filtrate obtained was put into a 10 ml vial and lyophilized. This gave a vial containing 30 mg of lyophilized polypeptide for use in injection.

As described above, this invention provides a novel polypeptide which has both the activities of cell-spreading and heparin-binding, and also provides a method for its preparation. This polypeptide acts to bind cells, with heparin sulfate and other components of the extracellular matrix, and it is useful for the treatment of wounds, to inhibit angiogenesis, and the like.

What we claim is:

1. A functional polypeptide which has the peptide structure of the following structural formula:

$$C_{277}(\text{Met})_n H_{271} - X \quad [I]$$

wherein $C_{277}$ is a sequence represented by the general formula:

1239
Pro Thr Asp Leu Arg Phe Thr Asn Ile Gly [II]
Pro Asp Thr Met Arg Val Thr Trp Ala Pro
Pro Pro Ser Ile Asp Leu Thr Asn Phe Leu
Val Arg Tyr Ser Pro Val Lys Asn Glu Glu
Asp Val Ala Glu Leu Ser Ile Ser Pro Ser
Asp Asn Ala Val Val Leu Thr Asn Leu Leu
Pro Gly Thr Glu Tyr Val Val Ser Val Ser
Ser Val Tyr Glu Gln His Glu Ser Thr Pro
Leu Arg Gly Arg Gln Lys Thr Gly Leu Asp
Ser Pro Thr Gly Ile Asp Phe Ser Asp Ile
Thr Ala Asn Ser Phe Thr Val His Trp Ile
Ala Pro Arg Ala Thr Ile Thr Gly Tyr Arg
Ile Arg His His Pro Glu His Phe Ser Gly
Arg Pro Arg Glu Asp Arg Val Pro His Ser
Arg Asn Ser Ile Thr Leu Thr Asn Leu Thr
Pro Gly Thr Glu Tyr Val Val Ser Ile Val
Ala Leu Asn Gly Arg Glu Glu Ser Pro Leu
Leu Ile Gly Gln Gln Ser Thr Val Ser Asp
Val Pro Arg Asp Leu Glu Val Val Ala Ala
Thr Pro Thr Ser Leu Leu Ile Ser Trp Asp
Ala Pro Ala Val Thr Val Arg Tyr Tyr Arg
Ile Thr Tyr Gly Glu Thr Gly Gly Asn Ser
Pro Val Gln Glu Phe Thr Val Pro Gly Ser
Lys Ser Thr Ala Thr Ile Ser Gly Leu Lys
Pro Gly Val Asp Tyr Thr Ile Thr Val Tyr
Ala Val Thr Gly Arg Gly Asp Ser Pro Ala
Ser Ser Lys Pro Ile Ser Ile Asn Tyr Arg
1515
Thr Glu Ile Asp Lys Pro Ser n is 1 or 0 and wherein $H_{271}$ is a sequence represented by the general formula:

1690
Ala Ile Pro Ala Pro Thr Asp Leu Lys Phe [III]
Thr Gln Val Thr Pro Thr Ser Leu Ser Ala
Gln Trp Thr Pro Pro Asn Val Gln Leu Thr
Gly Tyr Arg Val Arg Val Thr Pro Lys Glu
Lys Thr Gly Pro Met Lys Glu Ile Asn Leu
Ala Pro Asp Ser Ser Ser Val Val Val Ser
Gly Leu Met Val Ala Thr Lys Tyr Glu Val
Ser Val Tyr Ala Leu Lys Asp Thr Leu Thr
Ser Arg Pro Ala Gln Gly Val Val Thr Thr
Leu Glu Asn Val Ser Pro Pro Arg Arg Ala
Arg Val Thr Asp Ala Thr Glu Thr Thr Ile
Thr Ile Ser Trp Arg Thr Lys Thr Glu Thr
Ile Thr Gly Phe Gln Val Asp Ala Val Pro
Ala Asn Gly Gln Thr Pro Ile Gln Arg Thr
Ile Lys Pro Asp Val Arg Ser Tyr Thr Ile
Thr Gly Leu Gln Pro Gly Thr Asp Tyr Lys
Ile Tyr Leu Tyr Thr Leu Asn Asp Asn Ala
Arg Ser Ser Pro Val Val Ile Asp Ala Ser
Thr Ala Ile Asp Ala Pro Ser Asn Leu Arg
Phe Leu Ala Thr Thr Pro Asn Ser Leu Leu
Val Ser Trp Gln Pro Pro Arg Ala Arg Ile
Thr Gly Tyr Ile Ile Lys Tyr Glu Lys Pro
Gly Ser Pro Pro Arg Glu Val Val Pro Arg
Pro Arg Pro Gly Val Thr Glu Ala Thr Ile
Thr Gly Leu Glu Pro Gly Thr Glu Tyr Thr
Ile Tyr Val Ile Ala Leu Lys Asn Asn Gln
Lys Ser Glu Pro Leu Ile Gly Arg Lys Lys
1960
Thr wherein X has the following structural formula:

Asp—Glu—Leu—Pro—Gln—Leu—Val—Thr—Leu—Pr- [IV]
o—
His—Pro—Asn—Leu—His—Gly—Pro—Glu—Ile—Leu—
Asp—Val—Pro—Ser—Thr [IV]

wherein X is either present or absent.

2. A pharmaceutical composition for the inhibition of angiogenesis containing an effective amount of the functional polypeptide of claim 1 and a pharmaceutically acceptable carrier.

* * * * *